US00PP16711P3

(12) United States Plant Patent
Olesen

(10) Patent No.: US PP16,711 P3
(45) Date of Patent: Jun. 27, 2006

(54) MINIATURE ROSE PLANT NAMED 'POULPAH022'

(50) Latin Name: *Rosa hybrida*
Varietal Denomination: Poulpah022

(75) Inventor: Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 157 days.

(21) Appl. No.: 10/961,001

(22) Filed: Oct. 7, 2004

(65) Prior Publication Data

US 2005/0235387 P1 Oct. 20, 2005

(51) Int. Cl.
*A01H 5/00* (2006.01)

(52) U.S. Cl. ..... Plt./118

(58) Field of Classification Search ..... Plt./118, Plt./119, 125, 126
See application file for complete search history.

*Primary Examiner*—Howard J. Locker

(57) ABSTRACT

A new miniature rose plant which has abundant, apricot flowers and attractive dark green foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'Poulpah022'.

SUMMARY OF THE INVENTION

The present invention constitutes a new and distinct variety of miniature rose plant which originated from a controlled crossing between the female parent, an un-named seedling, and the male parent 'Korstoffein' described and illustrated in U.S. Plant Pat. No. 11,242, issued on Feb. 22, 2000. The two parents were crossed and the resulting seeds were planted in a controlled environment. The new variety is named 'Poulpah022'.

The new rose may be distinguished from its seed parent, an un-named seedling, by the following combination of characteristics:

1. The seed parent has a petal count of 30 petals, while 'Poulpah022' has 50 petals.
2. The seed parent has a general tonality of Yellow-Orange 18 C while 'Poulpah022' has a general tonality of Yellow 13 D to Yellow-Orange 16 B.

The new variety may be distinguished from its pollen parent, 'Korstoffein' by the following combination of characteristics:

1. While the pollen parent has 25 to 30 petals, the claimed plant has 50 petals.
2. While innermost petals of the pollen parent are Yellow-Orange 21C, those of 'Poulpah022' are Yellow 10 B to 11 A.
3. Bloom diameter of 'Korstoffein' is smaller than that of 'Poulpah022'.

The objective of the hybridization of this rose variety for commercial culture was to create a new and distinct variety with unique qualities, such as:

1. Uniform and abundant apricot flowers;
2. Vigorous and compact growth;
3. Year-round flowering under glasshouse conditions;

4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah022' from all other varieties of which he is aware.

As part of the rose development program, Mogens N. Olesen germinated the seeds from the aforementioned hybridization and conducted evaluations on the resulting seedlings in a controlled environment in Fredensborg, Denmark.

'Poulpah022' was selected by the inventor as a single plant from the progeny of the hybridization in the year 2000.

Asexual reproduction of 'Poulpah022' by cuttings and traditional budding was first done by Mogens N. Olesen in the nursery in Fredensborg, Denmark in June 2001. This initial and other subsequent propagations conducted in controlled environments have demonstrated that the characteristics of 'Poulpah022' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpah022'. Specifically illustrated in the drawing:

FIG. 1.1; Pedicel, receptacle, sepals, and reproductive parts;

FIG. 1.2; Sepals detached;

FIG. 1.3; Open flower and detached flower petals;

FIG. 1.4; Flower bud closed, ¼ open and open;

FIG. 1.5; Bare stem;

FIG. 1.6; Juvenile leaves exhibiting anthocyainin;

FIG. 1.7; Mature leaves.

DETAILED DESCRIPTION OF THE VARIETY

The following is a description of 'Poulpah022', as observed in its growth in a glasshouse located in Burlington, Ontario, Canada. Observed plants are 4 months of age, and were cultivated in a 15 cm pot. Color references are made using The Royal Horticultural Society (London, England) Colour Chart, 1995, except where common terms of color are used.

For a comparison, several physical characteristics of the rose variety, 'Poulnil', a rose variety from the same inventors described and illustrated in U.S. Plant Pat. No. 13,301 issued on Dec. 3, 2002 are compared to 'Poulpah022' in Chart 1.

CHART 1

| | 'Poulpah022' | 'Poulnil' |
|---|---|---|
| General Tonality | Yellow 13D to Yellow Orange 16B | Red-Purple 62D at margins, Red Group 36D in middle and basal zones, all with a faint overlay of green-Yellow 1B-C. |
| Petalage | 50, 7 to 10 of which are petaloids. | 16 to 19 petals. |
| Flower diameter | 60 mm | 65 to 75 mm |

FLOWER AND FLOWER BUD

Blooming habit: Continuous.

Flower bud:

*Size.*—Upon opening, 21–24 mm in length from base of receptacle to end of bud. 12 mm in diameter.

*Bud form.*—Ovate.

*Bud color.*—As sepals unfold, petals are Yellow Group 13A.

*Sepals.*—Upper Surface: Color: Green Group 138A to 138B. Texture: Medium pubescence observed. Lower surface: Color: Yellow-Green Group 144A. Texture: Smooth. Shape: Sepal apex is cirrhose. Base is flat at union with receptacle. Margins: Margins have strong foliaceous appendages on three of the five sepals. Size: 25 to 35 mm long by 15–18 mm wide.

*Receptacle.*—Surface Texture: Smooth. Shape: Urn-shaped. Size: On average, 7 mm in height by 7 mm wide. Color: Yellow Green Group 144B.

*Peduncle.*—Surface: Somewhat rough with small prickles. Length: 45 mm average length. Diameter: 2.75 mm on average. Color: Yellow-Green Group 144B. Strength: Medium strength. Upright.

*Borne.*—Singly.

Flower bloom:

*Fragrance.*—Moderate floral scent.

*Duration.*—As a pot plant, flowers last from 15 to 18 days. After flowers have fully matured, petals fall cleanly away from plant.

*Size.*—For a 15 cm pot rose, average flower diameter is 60 mm when open. Depth is generally 35 mm.

*Form.*—When flowers first open, flower petals remain tightly packed at the center with margins reflexing strongly. Flowers continue to open in imbricated fashion. Shape of flower when viewed from the side: Upon opening, the upper and lower parts resemble a flattened convex. After opening, the upper part is a flattened convex. The lower part is concave.

*Petalage.*—Under normal conditions, there are an average of 50 petals, 7 to 10 of which are petaloids.

Color:

*Upon opening, petals.*—Outermost petals: Upper surface: Yellow Group 11 D at the apex. Darkening to Yellow Group 11 B at the middle zone and Yellow Group 13 B at the basal zone. Lower surface: Yellow-Orange Group 16 B. At the apex, lighter coloration is Yellow-Orange 16 D. Innermost petals: Upper surface: Yellow Group 10 B to Yellow Group 11 A. Lower surface: Yellow-Orange Group 16 B. At the apex, lighter coloration is Yellow-Orange 16 D.

*Upon opening, basal petal spots.*—Outer and inner petals: Upper surface: Yellow Group 6 A. Lower surface: Yellow Group 4 B.

*After opening, petal color.*—Outermost and innermost petals: Upper surface: Yellow Group 11 C at the marginal zone, becoming 11 B at the middle zone, and 11 A at the basal zone. Lower surface: Yellow-Orange Group 20 B with intonations of Orange Group 24C.

*After opening, basal petal spots.*—Outermost and innermost petals: Upper and lower surface are Yellow Group 2 B.

General tonality: On open flower Yellow Group 13 D to Yellow-Orange 16 B. No change in the general tonality at the end of the $10^{th}$ to $15^{th}$ day. Afterwards, general tonality becomes Yellow Group 8 C.

Petals:

*Petal reflex.*—Strong.

*Petal margin.*—Entire and uniform.

*Shape.*—Generally broad elliptical. Base Shape is occasionally acute, but normally obtuse. Apex Shape is rounded.

*Size.*—30 mm in length by 25 mm wide on average.

*Thickness.*—Average.

*Arrangement.*—Not formal.

Petaloids:

*Quantity.*—7 to 10.

*Size.*—21 mm long; 9 mm wide.

*Shape.*—Narrow elliptical. Base is acute. Apex is rounded.

*Color.*—Upper surface: Yellow Group 11 C at the marginal zone, becoming 11 B at the middle zone, and 11 A at the basal zone. Lower surface: Yellow-Orange Group 20 B with intonations of Orange Group 24C.

Reproductive organs:

*Pollen.*—None observed.

*Anthers.*—Size: 3 mm long. Color: Yellow Group 10 A. Quantity: 60 on average.

*Filaments.*—Color: Yellow Group 13 A. Length: 4 mm.

*Pistils.*—Length: 7 mm long. Quantity: 45 on average.

*Stigmas.*—Superior relative to the length of the filaments and the height of the anthers. Color: Yellow-Green Group 154D.

*Styles.*—Color: Yellow-Green Group 154D.

*Seed formation.*—No seeds observed.

PLANT

Plant growth: Vigorous, compact, upright and bushy. When grown as a 15 cm pot plant on its own roots, the average height of the plant itself is 25 cm and the average width is 25 cm.

Stems:

*Color.*—Young wood: Yellow-Green Group 146 A. Older wood: Yellow-Green Group 146 A.

*Internodal distance.*—35 mm between nodes.

*Length of stems.*—20 cm on average from the base of the plant to the flowering portion.

*Stem diameter.*—Generally 3 mm.

*Surface texture.*—Young wood: Smooth. Older wood: Smooth.

Thorns: Incidence: Normally, 4 to 6 per 10 cm of stem. Size: Average length is 4 mm. Color: Mature and juvenile thorns are Greyed-Orange 173 C. Shape: Linear.

Plant foliage: Normal number of leaflets on normal leaves in middle of the stem: 5 to 7 leaflets.

*Compound leaf size.*—90 mm (l)×70 mm (w).

*Quantity.*—4 leaves per 10 cm of stem.

*Color.*—Juvenile foliage: Upper Leaf Surface is Yellow-Green Group 144A. Anthocyanic pigments the color of Greyed-Purple 183B appear at the margins. Lower Leaf Surface is Yellow Green Group 144 C. Anthocyanin the color of Greyed-Purple 184 A is generalized throughout the leaflet. Mature foliage: Upper Leaf Surface is Yellow-Green Group 147 A. Lower Leaf Surface is Yellow-Green Group 147 B.

Plant leaves and leaflets:

*Stipules.*—Size: 9 mm in length. Shape: Linear, slightly broad based with outward extending apices. Margins: Finely serrated with few stipitate glands. Color: Yellow-Green Group 144 A.

*Petiole.*—Length: 20 mm on average. Diameter: 2 mm. Color: Upper surface is Yellow-Green Group 146 A. Lower surface is Yellow-Green Group 144 B. Underneath: Small prickles observed. Upper Surface: Few stipitate glands observed.

*Rachis.*—Size: 40 mm in length. Color: Upper surface is Yellow-Green Group 146 A. Lower surface is Yellow-Green Group 144 B. Underneath: Small prickles observed. Upper Surface: Few stipitate glands observed.

*Leaflet.*—Size: 40 mm in length by 30 mm wide. Margins: Serrate. General Shape: Ovate. Apex Shape: Acuminate. Base Shape: Round. Texture: Smooth. Thickness: Average to somewhat thin. Arrangement: Odd pinnate. Venation: Reticulate. Leaf Gloss: Slightly glossy.

Disease resistance: Average resistance to mildew, black spot, and *Botrytis* under normal growing conditions in Burlington, Ontario, Canada, and Fredensborg, Denmark.

Cold hardiness: Plants have been found to be cold tolerant to USDA zone 7.

It is claimed:

1. A new and distinct variety of rose plant of the miniature class named 'Poulpah022', described and illustrated herein as a distinct and novel rose variety due to its abundant, apricot flowers, vigorous growth, compact habit, suitability for production from softwood cuttings in pots, and durable flowers and foliage which make the variety suitable for distribution in the floral industry.

* * * * *

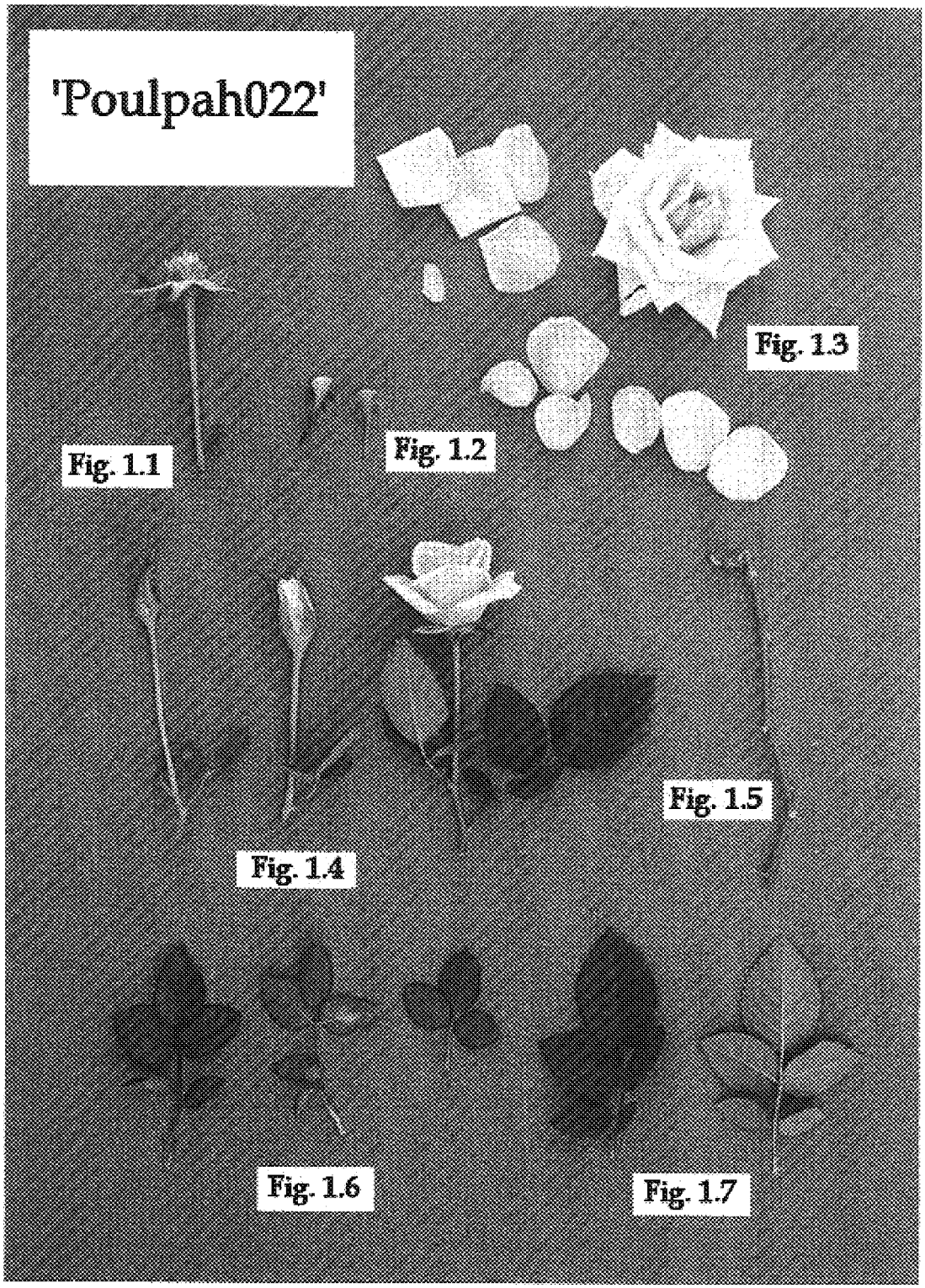
'Poulpah022'
Fig. 1.1
Fig. 1.2
Fig. 1.3
Fig. 1.4
Fig. 1.5
Fig. 1.6
Fig. 1.7